(12) United States Patent
Knobel et al.

(10) Patent No.: US 8,320,612 B2
(45) Date of Patent: Nov. 27, 2012

(54) SYSTEM AND METHOD FOR THE CONTACTLESS DETERMINATION AND MEASUREMENT OF A SPATIAL POSITION AND/OR A SPATIAL ORIENTATION OF BODIES, METHOD FOR THE CALIBRATION AND TESTING, IN PARTICULAR, MEDICAL TOOLS AS WELL AS PATTERNS OR STRUCTURES ON, IN PARTICULAR, MEDICAL TOOLS

(75) Inventors: Bruno Knobel, Laufen (CH); Charles Findeisen, Wettingen (CH); Frank Bartl, Neuenburg (DE); Erwin Keeve, Bonn (DE); Karl-Heinz Widmer, Schaffhausen (CH); Christoph Hämmerle, Zürich (CH)

(73) Assignee: Naviswiss AG, Laufen (CH)

( * ) Notice: Subject to any disclaimer, the term of this patent is extended or adjusted under 35 U.S.C. 154(b) by 1247 days.

(21) Appl. No.: 11/921,779

(22) PCT Filed: Jun. 8, 2006

(86) PCT No.: PCT/EP2006/005498
§ 371 (c)(1),
(2), (4) Date: Apr. 9, 2008

(87) PCT Pub. No.: WO2006/131373
PCT Pub. Date: Dec. 14, 2006

(65) Prior Publication Data
US 2009/0068620 A1  Mar. 12, 2009

(30) Foreign Application Priority Data

Jun. 9, 2005   (DE) .......................... 10 2005 026 654
Nov. 28, 2005  (DE) .......................... 10 2005 056 897
Nov. 29, 2005  (DE) .......................... 10 2005 057 237
Dec. 23, 2005  (DE) .......................... 10 2005 062 384

(51) Int. Cl.
*G06K 9/00* (2006.01)
(52) U.S. Cl. ..................................... 382/103; 348/169
(58) Field of Classification Search ................. 382/100, 382/128, 129, 130, 131, 132; 128/922; 378/4–27
See application file for complete search history.

(56) References Cited

U.S. PATENT DOCUMENTS

| 4,173,228 A | 11/1979 | Van Steenwyk et al. |
| 5,676,673 A | 10/1997 | Ferre et al. |
| 6,925,339 B2 | 8/2005 | Grimm et al. |

(Continued)

FOREIGN PATENT DOCUMENTS

AT  EP1523951  *  4/2005

(Continued)

OTHER PUBLICATIONS

International Search Report.

(Continued)

*Primary Examiner* — Anand Bhatnagar
(74) *Attorney, Agent, or Firm* — Collard & Roe, P.C.

(57) ABSTRACT

In order to develop known tracking systems, in particular in the medical field, the invention proposes a device for the contactless determination and measurement of a spatial position and/or spatial orientation of bodies using a tracking system, by means of which the bodies are located and brought into relation with one another, the tracking system, or at least components or modules thereof, being mobile.

35 Claims, 6 Drawing Sheets

U.S. PATENT DOCUMENTS

Figure 1:
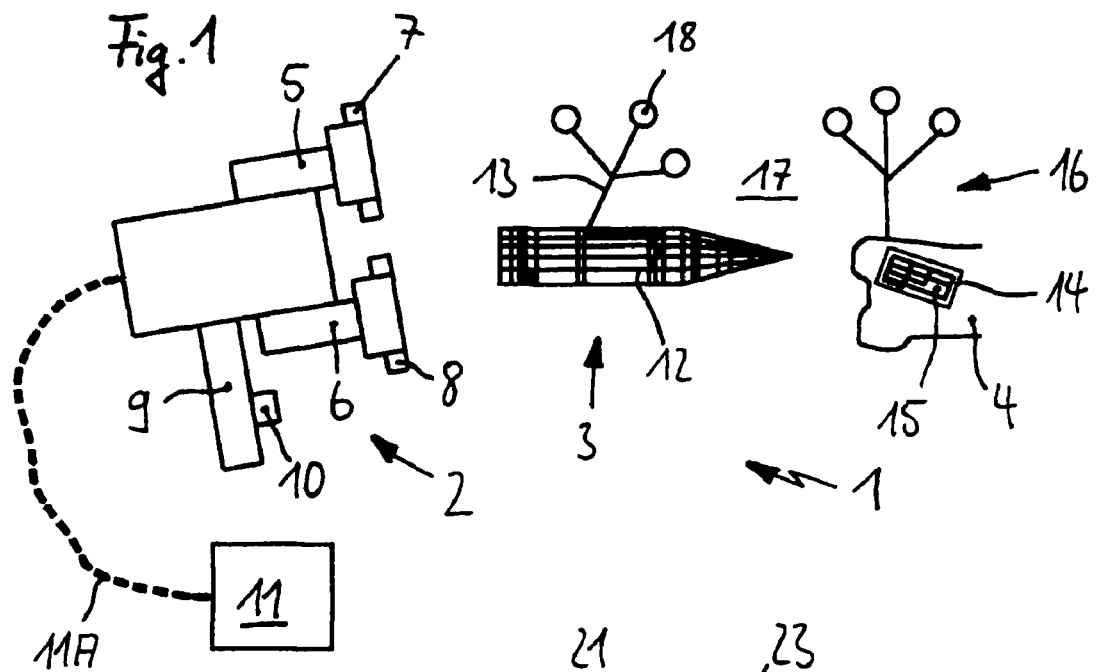

| | | | |
|---|---|---|---|
| 7,065,393 B2 * | 6/2006 | Sati et al. | 600/407 |
| 7,139,418 B2 | 11/2006 | Abovitz et al. | |
| 7,522,701 B2 * | 4/2009 | Jensen et al. | 378/62 |
| 7,581,191 B2 * | 8/2009 | Rice et al. | 715/764 |
| 7,831,082 B2 * | 11/2010 | Holsing et al. | 382/131 |
| 7,844,317 B2 * | 11/2010 | Salla et al. | 600/407 |
| 7,912,258 B2 * | 3/2011 | Warmath et al. | 382/128 |
| 2002/0188194 A1 * | 12/2002 | Cosman | 600/426 |
| 2005/0015099 A1 | 1/2005 | Momoi et al. | |
| 2005/0049485 A1 | 3/2005 | Harmon et al. | |
| 2010/0041985 A1 * | 2/2010 | Simon et al. | 600/426 |

FOREIGN PATENT DOCUMENTS

| | | |
|---|---|---|
| DE | 196 39 615 | 4/1998 |
| DE | 10 2004 001 858 | 5/2005 |
| EP | 0 672 389 | 9/1995 |
| EP | 1 523 951 | 4/2005 |
| JP | 2000-116670 | 4/2000 |
| JP | 2002-507735 | 3/2002 |
| JP | 2004-500187 | 1/2004 |
| JP | 2004-519271 | 7/2004 |
| JP | 2004-237101 | 8/2004 |
| JP | 2005-030911 | 2/2005 |
| JP | 2005-066345 | 3/2005 |
| WO | WO 01/54558 | 8/2001 |
| WO | WO 2005/032390 | 4/2005 |
| WO | WO 2005/076033 | 8/2005 |

OTHER PUBLICATIONS

Japanese Office Action dated Oct. 18, 2011 in Japanese Patent Application No. 2008-515141 with English translation of same.

European Search Report dated Sep. 19, 2011 in European Patent Application No. 10 01 1069 with English translation of relevant parts.

* cited by examiner

SYSTEM AND METHOD FOR THE CONTACTLESS DETERMINATION AND MEASUREMENT OF A SPATIAL POSITION AND/OR A SPATIAL ORIENTATION OF BODIES, METHOD FOR THE CALIBRATION AND TESTING, IN PARTICULAR, MEDICAL TOOLS AS WELL AS PATTERNS OR STRUCTURES ON, IN PARTICULAR, MEDICAL TOOLS

CROSS REFERENCE TO RELATED APPLICATIONS

Applicants claim priority under 35 U.S.C. §119 of German Application No. 10 2005 026 654.1 filed Jun. 9, 2005, German Application No. 10 2005 056 897.1 filed Nov. 28, 2005, German Application No. 10 2005 057 237.5 filed Nov. 29, 2005, and German Application No. 10 2005 062 384.0 filed Dec. 23, 2005. Applicants also claim priority under 35 U.S.C. §365 of PCT/EP2006/005498 filed Jun. 8, 2006. The international application under PCT article 21(2) was not published in English.

The invention concerns a system as well as a method of contactless determination and measurement of a spatial position and/or spatial orientation of bodies with a tracking system, by means of which the bodies can be localized and brought into relation with one another. The invention also concerns a method of calibrating primarily medical tools, medical components and/or medical instruments and a method of testing primarily medical tools, medical components and/or medical instruments for the presence of existing deformations. Moreover the invention concerns patterns on or structures at medical tools, medical components and/or medical instruments.

Systems and methods for the contactless determination and measurement of a spatial position and/or a spatial orientation of bodies are known for computer assisted surgery. In these interventions, navigation systems which are at least partially based on optical tracking systems are implemented. Common tracking systems acquire a position, in particular the position and/or orientation of instruments and body parts equipped with locators, with known mathematical methods in real time.

For example, patent application publication DE 196 39 615 A1 describes a neuro-navigation system which features a reflector referencing system with passive reflectors and with a marker system which comprises a mark or landmark. The reflectors and marks are arranged on the body parts to be treated and on the surgical instruments in such a fashion that their localization is unproblematically possible with a computer and camera unit. The position or data concerning the position can be displayed on a graphical monitor.

The computer and camera unit is stationary relative to the body parts which are to be treated. With the aid of further data which can be acquired with, for example, computer tomography, the relevant anatomy of the patient can be further acquired. Reflectors or marks which are arranged on the patient can support these functions by allowing the position of the patient to be acquired. With the thus acquired data, the position of the surgical instruments in use can be tracked and corrected, if necessary. The neuro-navigation system described in the state of technology allows a good and accurate guidance of the surgical instruments. The relatively large apparative effort is disadvantageous, as it can be disturbing during surgery treatment. This is especially relevant in cramped circumstances.

The task of the presented invention is to enhance known tracking systems so that their usage is significantly simplified.

The task of the invention is fulfilled by using equipment designed to acquire and measure the position and/or orientation of bodies in a contactless fashion with a tracking system for localizing the bodies and bringing into relation with one another by means of the tracking system or at least parts of it are mobile.

All currently known tracking systems are stationary and are fixed a certain distance from the field of operation on stable supports and are thus fixed compared to the body which position is to be acquired. The systems cannot be pumped again during the measurements in order to not negatively influence the measurement results. This can lead to problems in cramped circumstances so that the known tracking systems can be impedimental, despite their amenities. This is also due to the fact that marks which are affixed to the bodies must always be visible to the tracking system, but can be covered by the surgeon or other personnel.

The constraint that the tracking system must be stationary during its operation or use is not necessary with the mobile tracking system of the invention.

In the context at hand, the term "stationary" describes a tracking system which is positioned in a fixed position, above all during its use; in other words it is not moved when it is in use. The use of the tracking system therefore lies in the actual "tracking" of a body. It is understood that a conventional tracking system is also repositionable. Such repositioning does not, however, occur during the tracking operation; rather, if necessary, it occurs before or after the tracking. Therefore, state-of-the-art tracking systems cannot be portably implemented like the tracking system of the invention.

Therefore, the invented mobile tracking system is fundamentally distinguishable from known tracking systems.

The designation "tracking system" describes, in connection with the invented system, a mechanism with which an body, particularly a medical tool, a medical component, a medical instrument, and/or a medical resource, can be optically identified and a relative movement between it and a further body can be pursued. The term "tracking system" refers in particular to the optics and sensors, as well as the pertinent apparatus setup so that at least parts or groups of parts of the tracking system, containing the optics and sensors, can be relocated with respect to the parts being tracked.

The term "body" describes, for the purpose of this invention, both general technical structures or objects as well as special technical structures or objects in the field of medicine, like, for example, medical tools, medical instruments, implants, or other technical resources which are used in the field of medicine. Furthermore, the term "body" refers to bodies, body parts, and body regions of organisms, in particular of patients.

Bodies, like for example medical tools, medical components, medical instruments, and/or implants can optionally be equipped with exchangeable and/or adjustable inserts as well as with inserts which are suitably equipped with structures and locators.

The term "technical resources" refers in particular to resources which are used to determine a relative spatial position of bodies in relation to each other. Technical resources associated with tracking systems in the field of medicine are, for example, locators, structures, landmarks, and patterns on bodies.

The terms "spatial position" and "spatial orientation" describe, in connection with the patent application at hand, the spatial position and orientation of a body, for instance in the coordinate system of the tracking system and/or a relative spatial position and orientation between two bodies.

The task of the invention is also fulfilled by using a method designed to acquire and measure the position and/or orientation of bodies with a tracking system for localizing the bodies and bringing into relation with one another by means that the tracking system is moved and relocated relative to a body during use either manually or automatically.

The tracking system of the invention can be moved by bodies, repositioned with respect to the bodies, or even temporarily laid aside, even during its use. Thus, in particular the disadvantages of known tracking systems mentioned above can be eliminated.

Both invented system as well as the invented method are very well suited to enhance and ameliorate tracking systems and tracking methods in the field of medicine. It is understood that the invented system and invented method are not limited to medical fields of application, but can be advantageously implemented in any situation where the determination of spatial positions of at least two bodies is beneficial and/or essential.

A preferred variant of the embodiment provides for the mobile tracking system to be held portably relative to the bodies during its operation or during its use.

This tracking system differs from conventional tracking systems in particular because of this. Conventional tracking systems must always be arranged in a fixed position relative to the bodies which are to be acquired, or at least have a reference to a fixed laboratory coordinate system.

It is advantageous that a user, for example a surgeon, can put the tracking system at hand aside if it is not required for a certain work phase. Through this the implementation of the tracking system becomes very flexible.

It is especially beneficial because the mobile tracking system is arranged or held portably relative to the bodies during its operation or during its use. Through this, the tracking system of the device can be implemented during a task only when and where it is needed. Otherwise, the tracking system is laid aside.

Thus, a preferred implementation variant provides for the mobile tracking system to be portably arranged in relation to the body.

The term "portable" describes, in the context at hand, the exact opposite of the term "stationary". Therefore, it is advantageous that the tracking system is not rigidly fixed relative to an entire field of work or a local field of work. In fact, the mobile tracking system itself is moved and relocated relative to the bodies which are to be detected during an operation.

One method variant based on this concept provides for the manual guidance of the tracking system during its use. Through this, a surgeon is able to decide himself where and when the tracking system shall be held in front of a local field of work.

The mobile tracking system is easy to operate while it is held, in particular manually, directly in front of the local field of work.

All known tracking systems acquire nearly everything in the whole field of work with the required high measurement accuracy which results in enormous computational efforts. The computational effort required to determine the spatial position and/or the spatial orientation of bodies is also favorably reduced, as, unlike so far, not the whole field of work but only the local field of work is acquired, which is of interest for example for an operation.

A further embodiment of the method provides for the solely intermittent acquisition of the spatial position and/or the spatial orientation between at least two bodies. Through this, the required computational effort is further reduced.

The term "intermittent", in the context at hand, refers to the fact that the mobile positioning system is not permanently located in front of a field of work. The mobile tracking system can, for example, only be held in front of the local field of work before a main treatment and after the main treatment (in order to create) a before and after view. This way, the mobile tracking system can be set aside in the mean time.

Hence, the invented tracking system can beneficially be implemented for the measurement or control solely before and after certain treatment steps. For this purpose, it is aligned in a favorable position and direction and relative to bodies which are, for example, equipped with locators or structures. The tracking system can acquire the spatial position of the bodies relative to each other as a snapshot. The tracking system can also plot the spatial position of the bodies with a sequence of snapshots so that it can, for example, study the dynamic behavior of body parts before, during, and after certain treatment steps. This approach has the substantial advantage, compared to stationary systems, that the entire field of work no longer has to be acquired with the demanded precision; rather, only the actual local field of work is acquired. A further advantage is that the position and the direction of measurement of the tracking system can be optimally chosen for each step. It is particularly advantageous for objects or bodies which are close together that very handy tracking systems with small geometrical dimensions can be used.

In order to be able to guide the tracking system by hand well, it is beneficial that the mobile tracking system has a handle with which the tracking system can be manually held and/or guided.

A further alleviation in the handling becomes evident when the mobile tracking system weighs less than 2 kg or less than 0.5 kg or less than 0.1 kg. With such low weight, the tracking system itself can be operated well even when used for a longer time period. Particularly mobile tracking systems which weigh less than 0.1 kg are especially favorably implementable in dental surgery and/or minimally invasive surgery.

In order to activate the tracking system only when it is needed, it is beneficial that the mobile tracking system has an activation apparatus which starts and carries through an acquisition and a measurement.

It is thus procedurally beneficial if the acquisition and/or the measurement is started with a manual activation apparatus.

It shall be understood that the activation apparatus can be designed in many ways. For example, the activation apparatus can be located on the handle in the form of a switch. One implementation variation provides for the activation apparatus to be in the form of a foot switch. This design allows the mobile tracking system to be built even more compactly, as pieces of groups of pieces belonging to a switch on the mobile tracking system can be left away.

A further implementation variation provides for the activation apparatus to have a means of voice control. Through this, a surgeon can operate the mobile tracking system especially comfortably.

In case the mobile tracking system is not held and guided only by hand, it is advantageous for the mobile tracking system to have an attachment mechanism to connect it to a movable guidance mechanism, like a manually movable arm and/or a robot arm. With such an attachment mechanism the attachment of the mobile tracking system onto additional holding mechanisms, like, for example, a holding arm which is movable during the tracking or a robot arm is substantially simplified.

The attachment mechanism can be shaped in such a way as to allow the mobile tracking system to be placed on an arm of a surgeon. It can be beneficial if the attachment mechanism allows the mobile tracking system to be attached to the patient's head or an other body part of the patient.

Furthermore, for a further enhanced operation of the mobile tracking system, it is advantageous for the mobile tracking system to be self-sufficient.

In this regard, it is beneficial for the mobile tracking system to possess a means of measuring a displacement of the mobile tracking system relative to the body.

In order to be able to keep the tracking system updated, it is beneficial for the evaluation to be executed in the software. Software is especially easy to be updated.

For the self-sufficient operation of the mobile tracking system it is beneficial for the mobile tracking system to possess an own energy source. The energy source can be a battery, an accumulator, or a fuel cell, for example.

The operation of the mobile tracking system is further simplified when the mobile tracking system possesses a means of communicating wirelessly.

In order for the mobile tracking system to be able to visually perceive, it is advantageous for the mobile tracking system to have one or preferably several cameras.

It is beneficial for the cameras to have area sensors. The measurement accuracy and redundancy is substantially enhanced by more than two area sensors.

A preferred embodiment variation provides for locators, structures, patterns, and/or secondary patterns.

The term "locators" describes in the context at hand a technical resource which is attachable to an other body. The other body is locatable by the mobile tracking system because of the locator. The spatial position of a body is unproblematically determinable by means of the locator.

The term "structure", in terms of this invention, describes a three-dimensional entity which possesses a pattern. A structure also constitutes a body in terms of this invention. The structure can, for example, take the form of a flat plate. The structure can be permanently or detachably mounted on another body. In some applications it can be beneficial for the structure itself to be a body part of another body. The structure can, for example, be a part of a medical instrument.

The pattern is preferably located on the surface of the structure. It can, however, also be attached to the structure in different ways. The design of a structure pattern is already determined when it is produced.

A "pattern", in terms of this patent application, is an entity which is made up of, for example, straight or bent lines of different width and length, circles, ellipses, triangles, and rectangles, or a combination of these. It is preferably located directly on the surface of a body, for example a structure. It is significant that the pattern is clearly distinguishable from the surface on which it is located.

The pattern differs from a structure, for example, in that it is essentially a two dimensional, not a three dimensional entity. This means that the pattern as an entity has a length and a width like, for example, a structure. Its thickness is, however, so negligible in relation to the thickness of a structure that in the context at hand it is considered to be a two dimensional entity. The thickness of a pattern on, for example, a structure, is reduced to the layer of color on the structure. A pattern can also consist of a combination of reflecting, absorbing, fluorescent, phosphorescent, or luminous materials. These materials are well suited especially in combination with visible light, infrared light, or ultraviolet light.

A portion of a pattern can aid in enhancing the efficiency of an algorithm of a mobile tracking system for the determination and the measurement of the spatial position and orientation. If a pattern is located on a structure, the pattern or a portion of it can serve as a means of identification of the structure. With the help of the pattern, the body which is identified by the structure containing the pattern can be identified, and it can be determined if it is a medical instrument or a medical tool. Hence, the pattern gives fundamental information about bodies obtained with the tracking system to the mobile tracking system.

Aside from the described patterns, a second type of pattern exists in the invention at hand, referred to as "secondary patterns". It is beneficial, particularly for the registration of bodies, when further patterns, called secondary patterns, which can be measured by other imaging systems like, for example, a CT-device or an other device which detects bones and teeth three dimensionally with the help of X-rays exist aside from the patterns identified by the mobile tracking system.

In the context at hand one refers to a pattern if it is acquired predominantly by the mobile tracking system. If a pattern is acquirable and resolvable by a further imaging system it is referred to as a secondary pattern. Therefore, the secondary pattern preferably consists of X-ray opaque and/or X-ray transparent materials. Secondary patterns can additionally be comprised of materials which can be detected and measured by MRI systems. A further example of a secondary pattern can be detected and measured by imaging systems based on the terahertz spectral range.

Depending on the type of imaging system, like a CT or an MRI system, the secondary patterns should be made up of straight or bent lines of different width and length, circles, ellipses, triangles, and rectangles, or a combination of these, which thickness do not fall below a critical layer thickness.

Furthermore, it is advantageous for the locators, structures, patterns, and/or the secondary patterns to be attached to a tool, a component, and/or an instrument. Through this the body is detectable by at least the mobile tracking system.

If locators, structures, patterns, and/or secondary patterns are attached to a person's body parts, like bones or joints, the former can be identified by at least the mobile tracking system.

It is furthermore beneficial for a pattern to consist of straight or bent lines of different width and length, circles, ellipses, triangles, and rectangles, or a combination of these which are detectable and suitable for the mobile tracking system.

In addition, it is advantageous for a pattern to consist of absorbing, non-reflecting, reflecting, fluorescent, phosphorescent, or further luminous materials.

One embodiment variation provides for a secondary pattern to be geometrically related to a pattern. It is particularly beneficial for a registration process when a well defined secondary pattern exists beside the pattern measured by the mobile tracking system. The secondary pattern, which is made up of suitable materials, is identified and measured by other imaging systems. If the secondary pattern consists of X-ray opaque and X-ray transparent materials it can be identified and spatially resolved by CT devices or other devices which can three dimensionally detect and resolve bones and teeth using X-ray radiation.

Thus, it is advantageous for a secondary pattern to be identifiable by further imaging systems, in particular non-optical ones.

Furthermore it is advantageous for a structure contains patterns with known position and/or geometric details. Through this, the mobile tracking system can exactly measure a body which contains the patterns.

In order to be able to favorably affix structures to bodies, it is advantageous for a structure to contain a means of being fixed to bodies.

In this regard it is beneficial for the fixing agent to have struts for affixing it to bodies.

It is also beneficial for the structure to be composed of a flat plate. A pattern can be applied particularly well onto a flat plate.

Such an implementation variation provides for the structure to be composed of a flat plate with a three dimensionally structured surface.

It is constructionally especially beneficial for the structure to be a part of a medical tool, a medical component and/or a medical instrument. Through this, the structure can be favorably integrated into a body.

A further advantageous attachment possibility results from the use of a magnet as a structure.

In order for a structure to always be well identifiable by the mobile tracking system it is advantageous for the structure to possess a dirt repellent surface.

In order to be able to identify bodies particularly well, particularly patterns on bodies or structures on bodies, it is advantageous for the mobile tracking system to feature a means of illumination.

Depending on the area of application it is beneficial for the means of illumination to feature lights of the hyper red range.

It is beneficial for the body to contain deformable elements. By means of the deformable elements, the body is versatilely adjustable and adaptable to any circumstances it comes across.

In order to be able to discover deformations of a body, for example a medical tool or medical instrument, it is particularly advantageous to identify and measure the geometry of a body. It does not matter if the deformations of the body are intended or unintended.

Furthermore, it is beneficial for the bodies to be registered by means of patterns and/or secondary patterns which are attached to the bodies and can be identified by imaging systems.

The attachment of the mobile tracking system to a body, particularly a medical tool and/or a medical instrument, allows for further simplification. The mobile tracking system is, for instance, temporarily attachable to a body part belonging to a patient, like a bone.

It is advantageous for the spatial position and/or the spatial orientation of locators attached to bodies to be detected and measured relative to structures and/or patterns attached to the bodies.

In order to be able to detect patterns on structures with the mobile tracking system which are not in the direct field of vision of the mobile tracking system, it is beneficial for the device to contain a mirror which features patterns and/or secondary patterns. The patterns which are not directly viewable by the mobile tracking system can be made viewable by means of the mirror. Because the mirror also contains a pattern and/or a secondary pattern its spatial position is determinable, particularly by the mobile tracking system. The spatial position of the patterns viewable using the mirror can be determined using the spatial position of the mirror.

The task of the invention is also fulfilled by using a method of calibrating particularly medical tools, medical components, and/or medical instruments. The medical tools, medical components, and/or medical instruments are furnished with patterns and/or structures which contain patterns. The medical tools, medical components, and/or medical instruments are measured by means of the patterns and/or structures. Through this, the effort needed to calibrate such bodies is considerably reduced.

The required mechanical accuracy, particularly concerning medical instruments, causes very high production costs in some cases. This is the case particularly for medical instruments with interchangeable inserts, the tips of which are furnished with a scalpel or probe tip.

If the medical instrument is used without being previously calibrated, the attainable accuracy of the spatial position results from the tolerance of the instrument fabrication. Additionally, the possibility that inadvertently deformed instruments are used is always present. With additional state-of-the-art calibration mechanisms, the geometry of the medical instruments are usually measured and tested before or between certain work phases with the optical tracking system. The invention provides possibilities that these additional calibration mechanisms may not be needed.

It is therefore beneficial for measuring the patterns and/or structures by a tracking system, particularly a mobile tracking system, in order to measure the shape of medical instruments.

The invention concerns in particular a calibration method with a device, with which the mobile tracking system measures the structure of the instrument or tool. This has the essential benefit that the customary calibration devices can be dispensed with or simplified.

The form of the structure and the characteristics of the pattern are defined during production. If the pattern is given, the essential geometric features of the structure are also known. Essential geometric features are, for example, diameter, length, or radius. If, for instance, the entire surface of an undeformed body is covered with a suitable pattern, the geometric form of the body can be adequately exactly described with a measurement of the pattern.

The spatial position of the locators relative to the structures is measured by the tracking system during the calibration procedure. It is therefore no longer necessary for the spatial position of the locators to be extensively realized during production. A typical calibration procedure can take place as follows.

The instrument is turns in the measurement volume or the work field of the tracking system so that all sides of the instruments are sequentially measured in the calibration mode. Alternatively, the tracking system itself can be guided around the instrument. Furthermore, the calibration mode comprises the recognition and analysis of structures, the determination of the geometry of structures, the allocation of the structure regarding the spatial shape of the instruments based on the identification as well as the spatial position of locators with regard to the structure or the spatial shape of the instrument.

This calibration procedure for an instrument or a tool can be repeated if necessary. Since both the structure (complete or partial) as well as the locators are identified during the measurement of the spatial position of the bodies, the calibration can take place concurrently or be verified periodically. The tracking system accordingly contains suitable algorithms to fulfill this task.

The task of the invention is also fulfilled by using a method of testing in particular medical tools, medical components and/or medical instruments regarding existing deformations. In order to achieve this, a mobile tracking system identifies patterns on medical tools, medical components, and/or medical instruments.

It is advantageous, if patterns on in particular medical tools, medical components, and/or medical instruments are used to calibrate and/or test for deformations of medical tools, medical components, and/or medical instruments.

The mobile tracking system is especially capable of measuring and detecting deformed instruments, as the current structure differs from the one defined during the identification or the one previously measured. The deformation can occur unintentionally for example before or during a work phase. The deformation can also be intentionally carried out in order to adapt the geometric form of an instrument for a procedure step, for example. The geometric shape of the deformed instrument in particular can be adequately accurately determined using the calibration method.

Furthermore, the mobile tracking system substantially supports the user in registering the individual bodies, in particular during a surgery, which represents a considerable simplification of a conventional registration procedure.

This simplification is achieved because on the one hand the tracking system detects a structure and/or a pattern on the respective body part and on the other hand the other imaging systems (C-Arm, CT, MRI and/or an other device which identifies bones and teeth three dimensionally using X-rays) detect the patient data and the secondary patterns and process this data as spatial information. Through this, the spatial position of a structure regarding the patient data is always known. For this reason, the time-consuming preoperative determinations of the registration points as well as the probing of these points with a pointing instrument measured by the tracking system can be omitted. The mobile tracking system preferably contains appropriately optimized algorithms in order to fulfill this task. This provides the further essential benefit that the tactile methods for the registration are ideally no longer required. Or the tactile method is employed for control purposes if necessary.

The task of the invention is also fulfilled by a method in which patterns and/or secondary patterns are attached to at least one suitable tooth or to a template which is attached to a suitable tooth or a structure which is attached to a jaw by means of which the spatial position and/or the relative spatial orientation of the patterns and/or the secondary patterns are determined relative to one another.

The invention at hand is therefore also particularly advantageous in the field of dental surgery.

In order to obtain further data about the area of surgery, it is beneficial for the surface of a local field of work to be optically scanned beforehand.

Further data about the area of surgery can be acquired when the local field of work is measured three-dimensionally using X-ray radiation.

A surgeon obtains a very accurate picture of the area of surgery when a three-dimensional model is established based on the acquired scan and X-ray data as well as the data acquired from a mobile tracking system of the system.

In order to establish the model, at least the acquired scan and X-ray data are using preferably the same coordinate system.

A preferred variant embodiment of the method uses the established model for determine a configuration of an implant and/or a crown.

A surgical treatment can be carried out particularly accurately if a relative spatial position and/or a relative spatial orientation of a drill, a drill axis, a drill depth and/or a drill position is determined by means of this model.

It is furthermore advantageous if the determined configuration of the crown is produced essentially simultaneously to the surgical drill procedure by means of CAD/CAM support.

In summary, the tracking systems pertaining to the invention are especially well suitable for identifying locators and structures attached to bodies, determining the spatial position of the locators and structures, and calculating the spatial position of the bodies using this data.

Furthermore, the tracking system is capable of determining the whole or a part of the geometric shape of bodies onto which suitable structures have been attached. Furthermore, it relates the geometric shape of the bodies to the locators attached to the bodies.

A spatial position of an body can be identified either with the locators or with the structure. The determination of the body's spatial position can also be carried out with both the locators and the structure.

The mobile tracking system at hand can be directly attached to an object or body, as well as on a tool, an instrument, or a further body part. The has the essential benefit that the spatial position of this body is known solely by means of the tracking system, without any further measurements.

A further advantage is that the number of required bodies in the field of work is reduced. In an extreme example, only the tool on which the mobile tracking system is attached is in use and locates a structure which is attached to a body part. An especially important example is the implementation in the field of dental surgery, in which the mobile tracking system is favorably integrated in or on a tool, for example a drill. The structures can be located on a template and/or on teeth. The templates are particularly stable when they are put over one or more teeth.

The mobile, lightweight, portable, and handily designed tracking system of the invention can be used to measure manually, as necessary. The spatial position before and after certain work phases can be measured with it. During the work phase it can be laid aside. The tracking system can, therefore, as already mentioned, be attached to a robot, in particular a robot arm, and conduct measurements only on demand.

The mobile tracking system at hand could, at least temporarily, be attached to a tripod for a long duration measurement of the spatial position of the bodies in the area of work. Important properties of the mobile tracking system, like the measurement volume, the measurement distance range, or the measurement accuracy are defined, among other things, by the layout and the properties of the cameras, the locators or the structures. The measurement accuracy, the measurement volume, and/or the measurement distance range substantially influence the geometry of the mobile tracking system and the layout and properties of the cameras. Small measurement volumes and small measurement distance ranges typically allow tracking systems which have small geometrical dimensions. Conversely, large measurement volumes and large measurement distance ranges usually lead to geometrically larger tracking systems. For the same measurement accuracy and using the same camera technology, the effort of larger tracking systems is significantly larger as that of smaller tracking systems.

At this point it should be pointed out that all of the instruments or tools, inserts, structures, locators, or parts thereof are preferably produced for a one-time use. In certain applications this is beneficial because of hygienic reasons, for example. Further advantages arise for logistics, cleaning, sterilizing, and testing of the bodies.

A further significant advantage is that such one-way pieces can be produced inexpensively using suitable materials and suitable manufacturing techniques, like for example injection molding or three-dimensional shaping techniques.

A further advantage is that the manufacturing accuracy of the locators including attachment can be reduced because the locator positions are measured relative to the structure with the mobile tracking system at hand.

The task of the invention is also accomplished by a method in which a first structure with pattern and/or a first locator is attached to a body, like, for example, a component and at least a further structure with patterns and/or at least a further locator is also attached to the body. The relative spatial position and/or the spatial orientation of the structures with the patterns and/or the locators are determined by means of the device of the underlying invention. The body is then treated. A relative spatial position and/or relative spatial orientation of the structures with the patterns and/or locators is again acquired during at least one further measurement. The spatial position and/or spatial orientation of the two measurements are compared to each other.

Advantageously, the state of a body or a body part before and after a work phase can be compared, especially concerning a spatial position.

An advanced method variant advantageously provides for the bodies to be processed stepwise until the position and orientation of the structures with the patterns and/or locators from the first measurement correspond to the position and orientation of the structures with the patterns and/or locators from the second measurement. The spatial position and/or spatial orientation is preferably acquired solely using the present patterns by means of the mobile tracking system.

Through this, the body or parts of the body can be aligned to the initial state with highest precision after a previous work phase.

A method variant favored in the field of medicine provides for a surgeon to work on a joint or an other body part of a patient.

If, for example, a part of a patient's joint is replaced with a prosthesis or if a bone is manipulated in order to insert an implant between two bone pieces, it is favorable for at least two structures with patterns to be suitably attached onto the sides of the joints and for the relative spatial position to one another to be determined by means of the patterns and the mobile tracking system before the actual main surgery begins. The surgeon replaces a piece of the joint between the two structures with a prosthesis. After the successful main surgery, the spatial position of the structures is redetermined and compared to the previously acquired spatial position. Through this, the surgeon has the verifiable security that the joint or pieces of it are again arranged in their original position or are medically sufficiently close to their original position.

Due to the particularly easy usage, the tracking system at hand is especially beneficially deployable in the fields of dental surgery and minimally invasive surgery.

Further benefits, objectives, and properties of the invention at hand are described by means of the following descriptions of the included drawings in which devices for the contactless determination and measurement of a spatial position and/or a spatial orientation of bodies with a tracking system as well as parts or groups of parts of such devices are depicted.

The figures show

Figure 2:
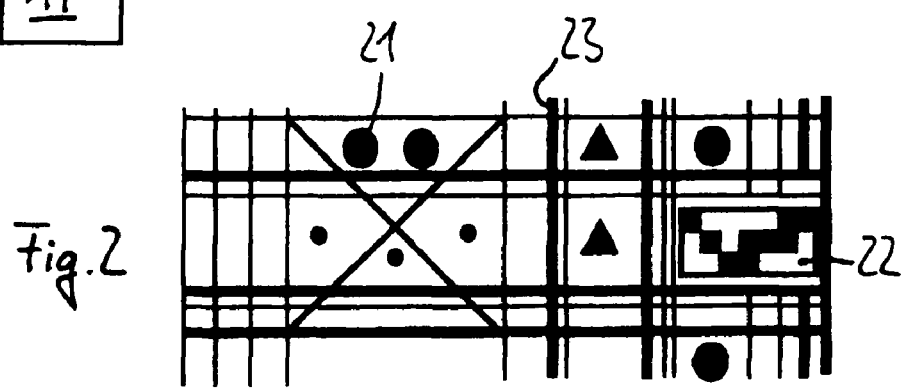
Figure 3:
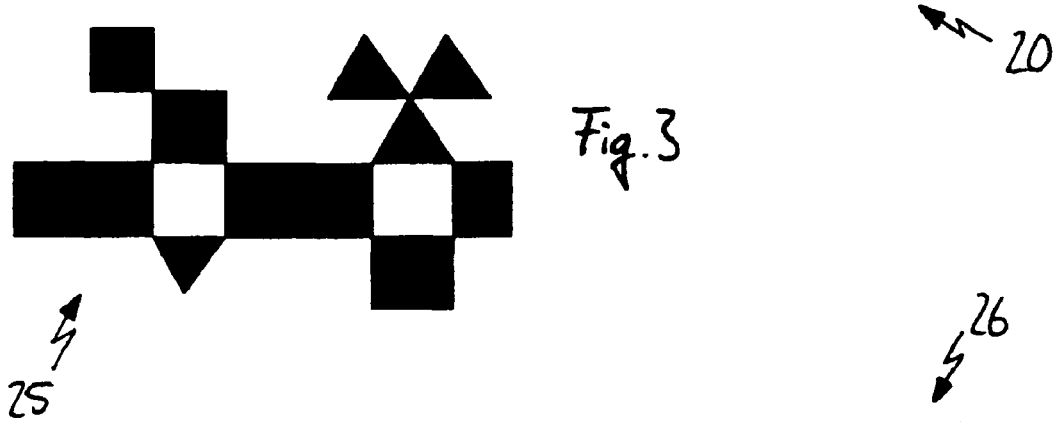
Figure 4:
Figure 5:
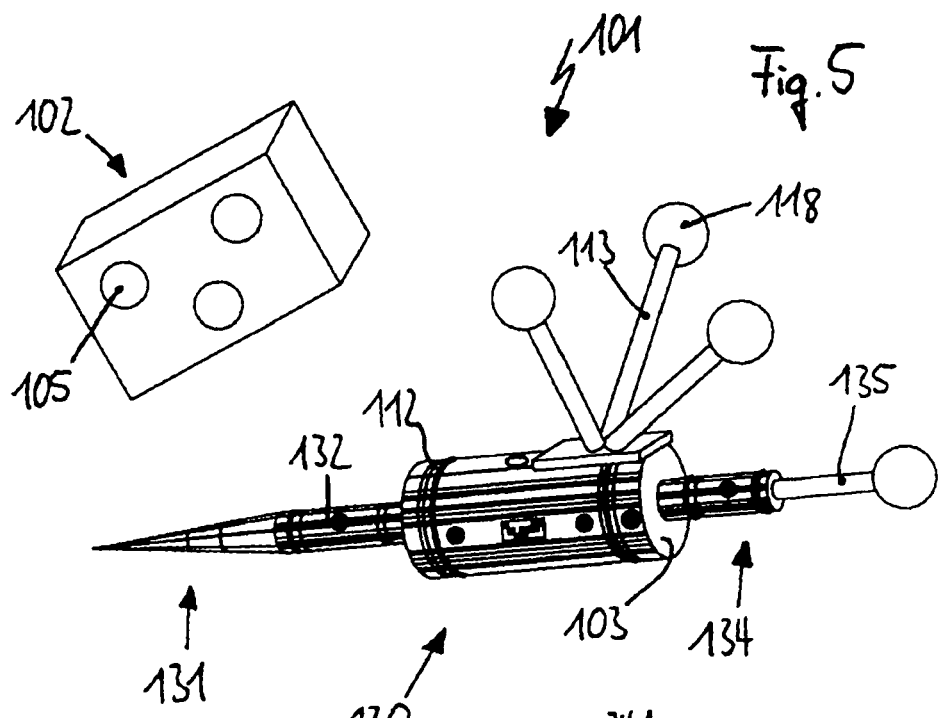
Figure 6:
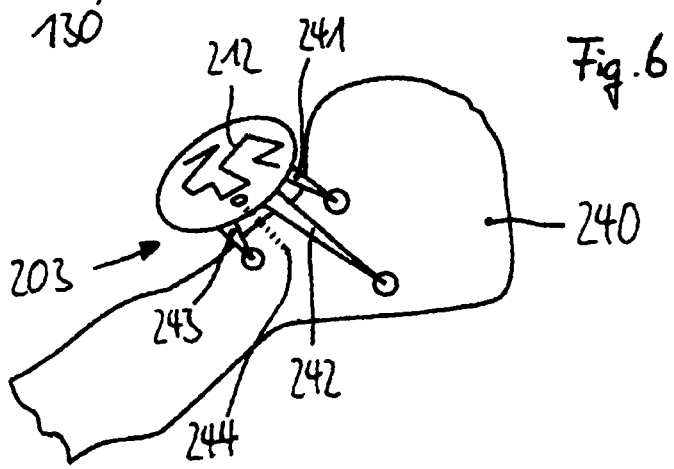
Figure 7:
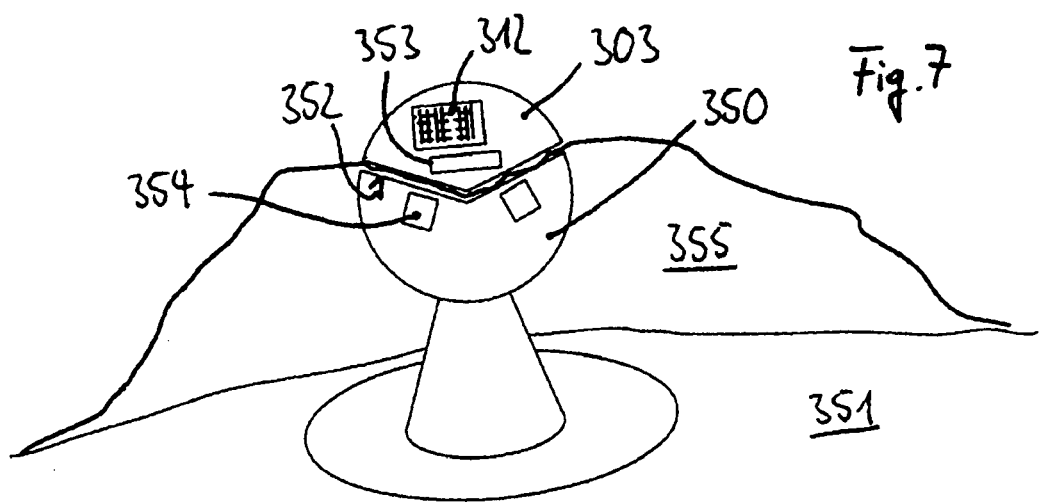
Figure 8:
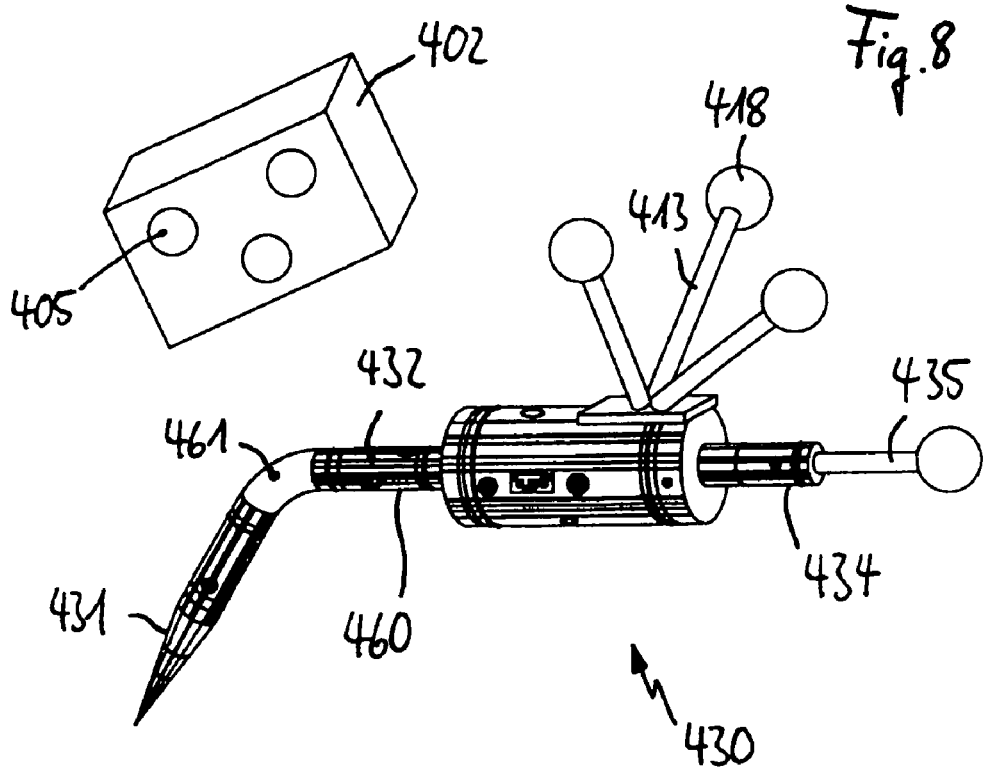
Figure 9:
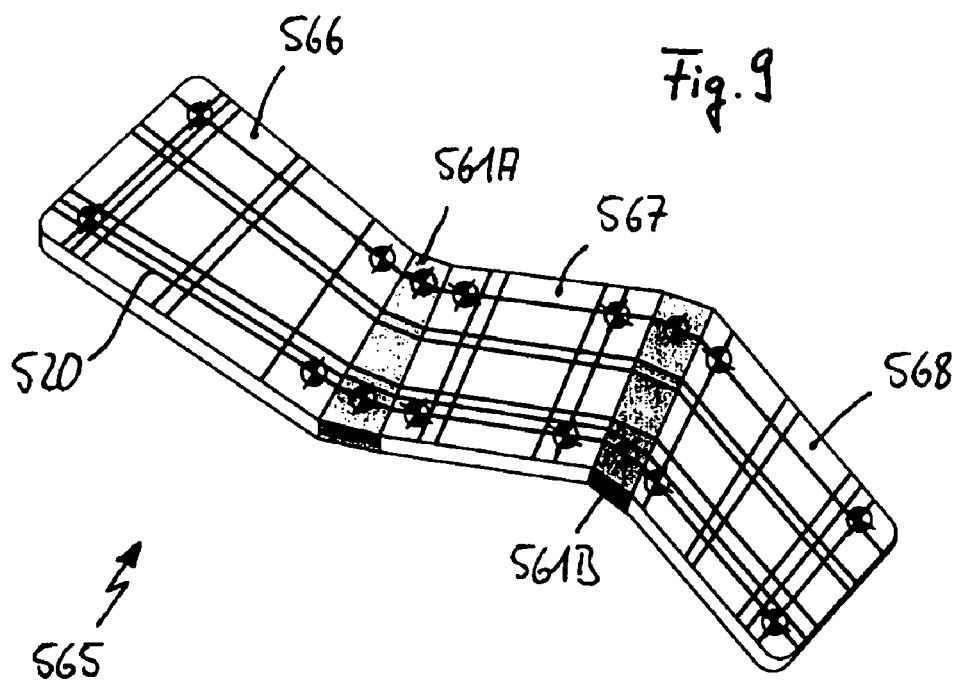
Figure 10:
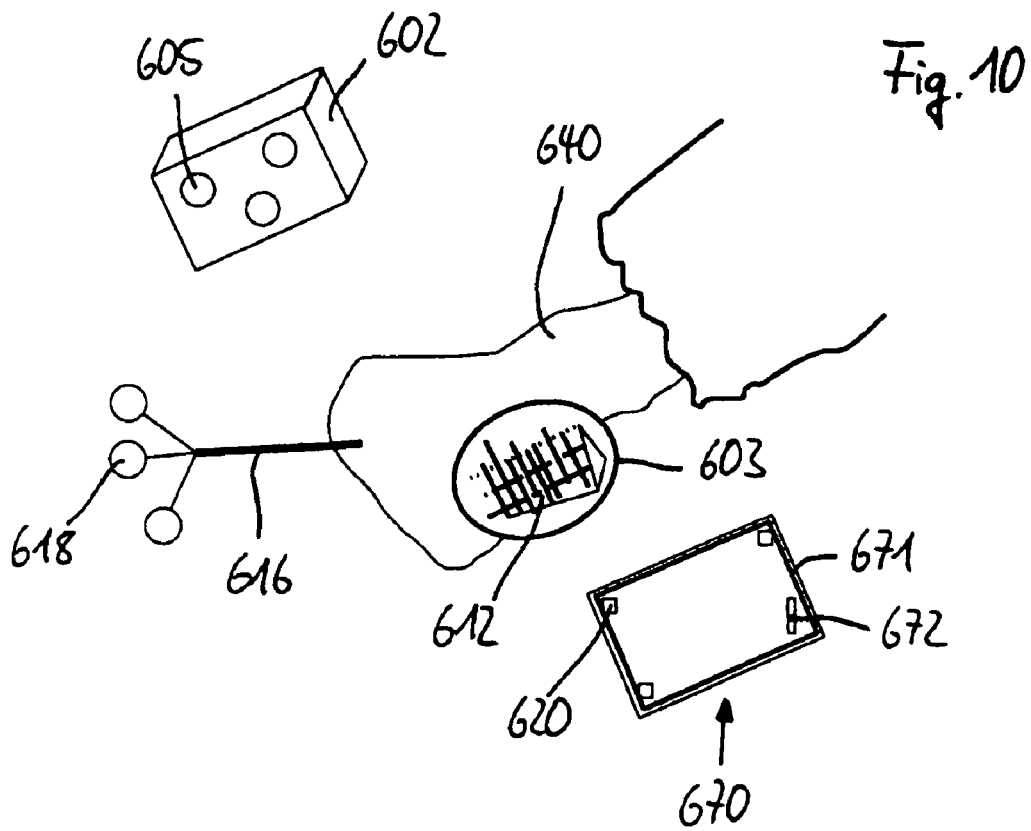
Figure 11:
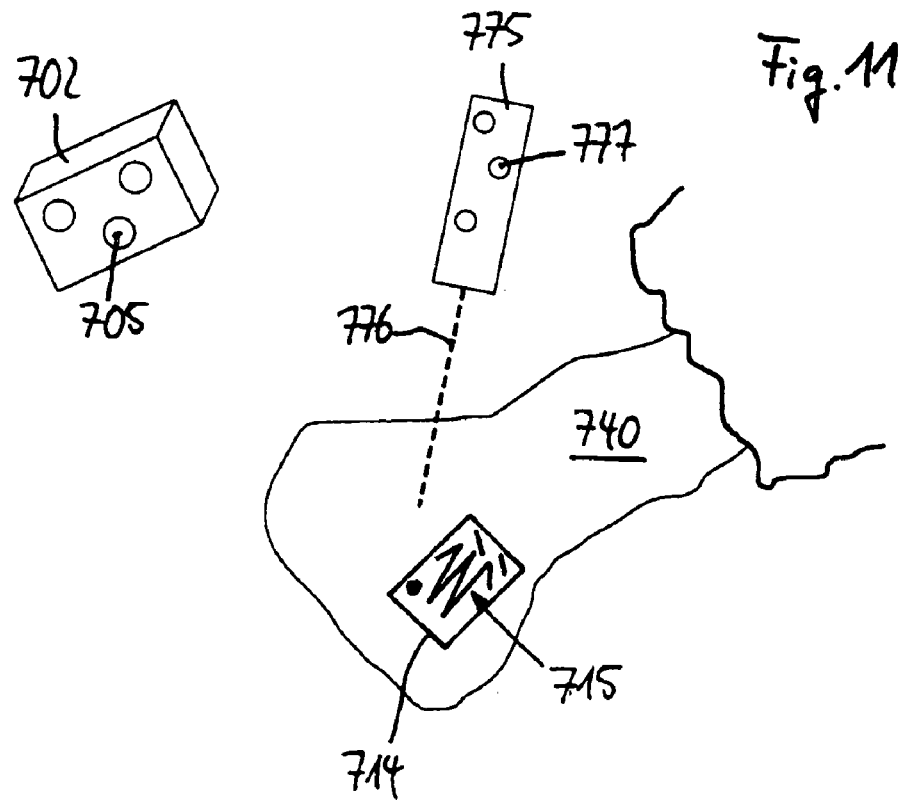
Figure 12:
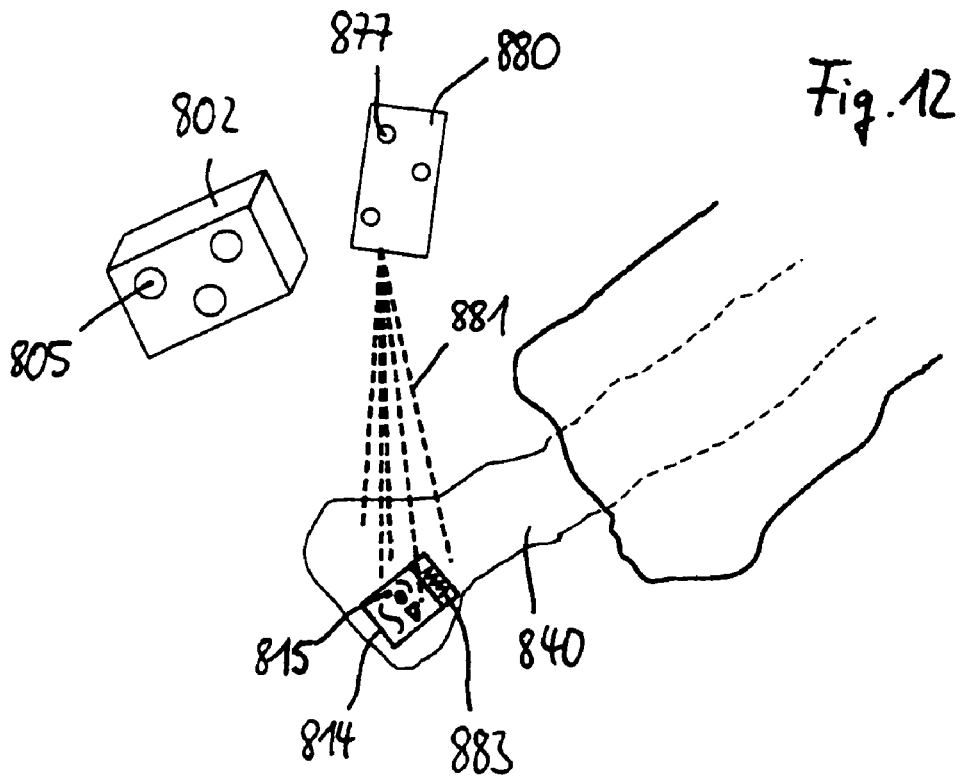
Figure 13:
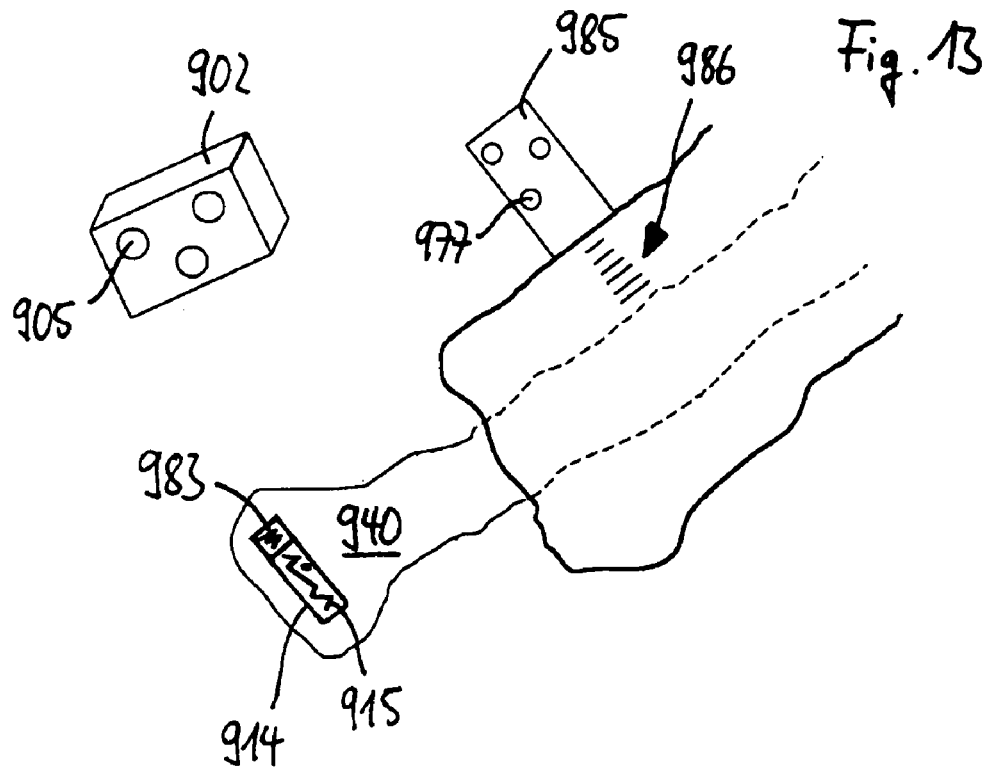
Figure 14:
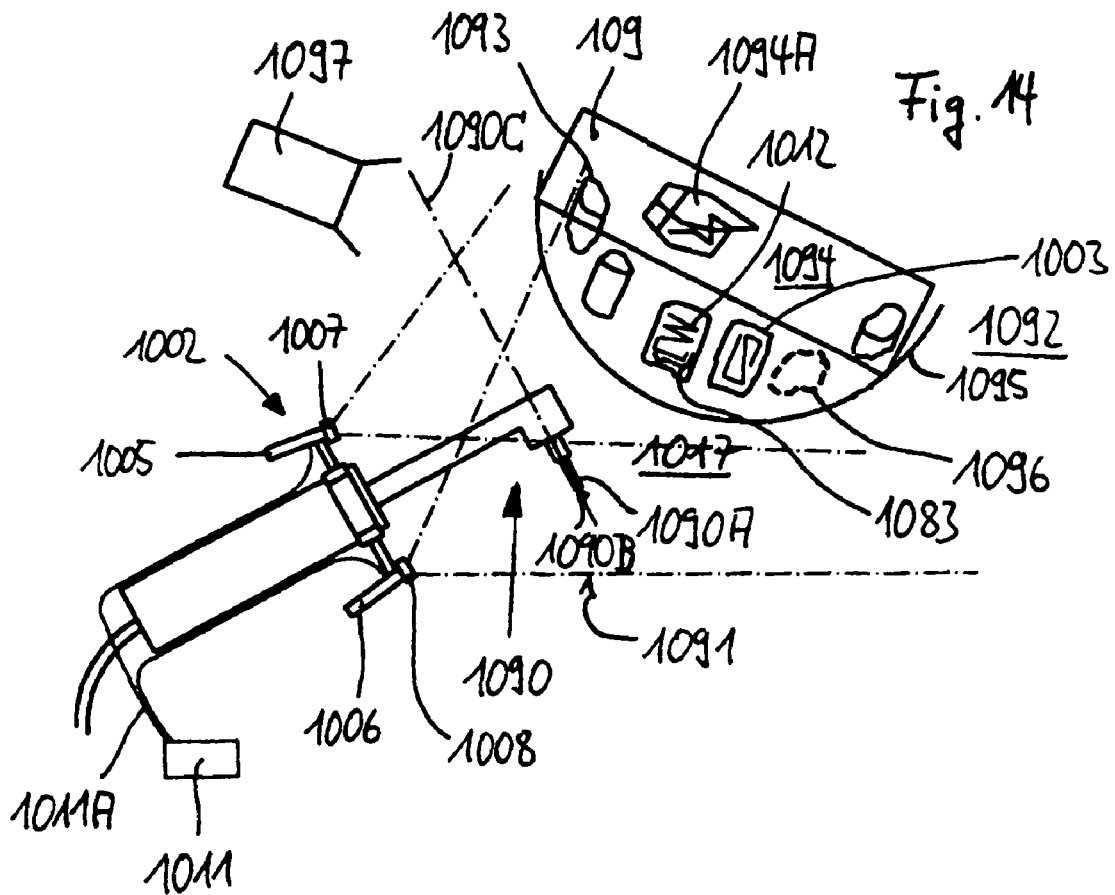
Figure 15:
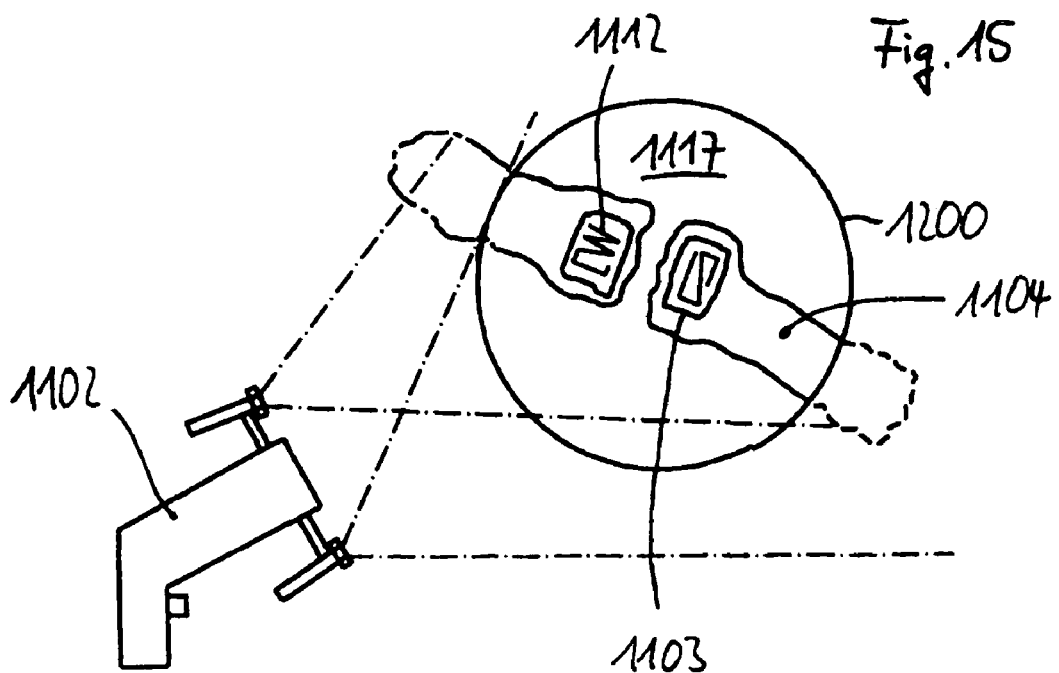

FIG. 1 schematically a layout of the device according to the invention with a mobile tracking system with a medical instrument including a structure with a pattern in front of a body part with another structure;

FIG. 2 schematically a possible embodiment of a first pattern;

FIG. 3 schematically a possible embodiment of a further pattern;

FIG. 4 schematically a further pattern example;

FIG. 5 schematically a layout consisting of a mobile tracking system and a medical instrument with locators, structures, and patterns;

FIG. 6 schematically a view of an attachment technique of structures on hard body parts;

FIG. 7 schematically a view of a funnel-shaped landmark with a spherical cap set on top which features patterns and magnetic materials;

FIG. 8 a schematic layout of a further mobile tracking system and a medical instrument with attached locators, structures, patterns, and a three-dimensionally deformable element;

FIG. 9 schematically a view of an implant with three-dimensionally deformable elements and a pattern;

FIG. 10 schematically a layout of a mobile tracking system, a body part with a structure and patterns, and a mirror system;

FIG. 11 schematically a layout of a mobile tracking system, a scanner, and a body part with an attached structure and patterns;

FIG. 12 schematically a layout of a mobile tracking system, a projector and a body part with an attached structure with patterns;

FIG. 13 schematically a layout of a mobile tracking system, an ultra-sound transducer, and a body part with an attached structure with patterns;

FIG. 14 schematically a layout of a drill and milling head, a device which three-dimensionally detects bones and teeth using X-ray radiation, and structures on a template and/or structures on teeth;

FIG. 15 schematically a layout of a mobile tracking system and two body parts which are equipped with structures.

Layout 1, shown in FIG. 1, encompasses a mobile tracking system 2, a medical structure 3, and a bone 4 as a human body part. The mobile tracking system 2 features a first camera 5 and a second camera 6.

In order to illuminate well the medical structure 3 and the bone 4, the mobile tracking system 2 features a first light 7 and a second light 8. Lights 7 and 8 have light emitting diodes (not exemplarily shown here) which emit in the infrared spectrum. Alternatively, light emitting diodes can be implemented which emit in the hyper-red spectrum.

In order to be able to hold and guide the mobile tracking system 2 well, it features a hand grip 9 to which, in this implementation example, an activation mechanism 10 is attached. By means of the activation mechanism 10 the type of measurement can be chosen. In FIG. 1, three measurement modes are available, namely a single measurement, a series of single measurements and/or a film sequence.

An evaluation and display device 11 is assigned to the mobile tracking system 2 and is connected to the mobile tracking system 2 with a communication connection 11A. The mobile tracking system 2 at hand is very light and therefore handy and easily portable.

The structure 3 features a first pattern 12 and a first locator 13. A further structure 14 with a second pattern 15 and a bone locator 16 is attached to bone 4. The structures 3 and 14 are three-dimensional bodies onto which the pattern 12 or the pattern 15 are attached. The patterns 12 and 15 allow the mobile tracking system 2 to determine the spatial position of structures 3 and 14. The mobile tracking system 2 can determine the geometry of the structure 3 above all with the pattern 12.

By means of the mobile tracking system 2, the local field of work 17, which contains the structure 3 and an interesting part of the shown bone 4, is acquired.

The mobile tracking system is supplied with energy through the communication connection 11A. It is understood that a wireless connection between the mobile tracking system 2 and the evaluation and display device 11 can be implemented in place of the wired communication connection 11A. In this case, the mobile tracking system 2 must have an own energy supply which it can carry with it, like, for instance, a battery or fuel cell.

Both the first locator 13 and the bone locator 16 are equipped with retro-reflective spheres 18. The shape of the first structure 3 and the further structure 14 as well as the properties of the first pattern 12 and the second pattern 15 are already defined during the production of structure 3 and the further structure 14. The mobile tracking system 2 can therefore exactly identify and explicitly allocate the properties of the first pattern 12 as well as the second pattern 15.

The surfaces of the structure 3 and the further structure 14 are designed in order to repel dirt. Through this, the measurement results of the mobile tracking system 2 are impaired less by contaminations, for example blood splatters or impure air. A probably necessary cleansing of the surface is substantially simplified by the dirt repellent surface.

Pattern 20, shown in FIG. 2, contains many lines of different widths, circles, ellipses, triangles, and rectangles. Some portions 21 of the pattern 20 are used to increase the algorithm efficiency of the mobile tracking system 2. An optional portion 22 of the pattern 20 is used to identify a structure which is assigned to pattern 20. In the portion 22, in particular the relationship between a structure and a medical instrument or a medical tool is defined.

Furthermore, the pattern 20 contains multiple lines 23 (numbered only exemplarily here) with different widths. The lines 23 beneficially have a sufficiently dimensioned width, here for example four to ten pixels of the camera sensor used, in order to determine a sensor image of pattern 20, and therefore also the structure geometry, with sufficient accuracy.

Advantageously, pattern 20 contains wide and thin lines 23, so that pattern 20 can always be recognized well. For example, if the focus length of the cameras is given and the distance between a body and a tracking system varies strongly during a phase of work, it is beneficial for the pattern 20 to be composed of lines of different widths. The wide lines of the pattern 20 are used above all over large distances by the mobile tracking system. The thinner lines of pattern 20, however, are used over smaller distances between a body and a mobile tracking system.

The further patterns 25 and 26, shown in FIG. 3 and FIG. 4, show the possible diversity of patterns which could implemented in the invention at hand.

Layout 101, according to FIG. 5, shows a mobile tracking system 102 in the immediate proximity of a medical instrument 130.

The mobile tracking system 102 features three cameras 105 (only exemplarily numbered here).

The medical instrument 130 is designed to be an insert to be attached to structure 103. The insert is inserted into the structure 103. The medical instrument 130 has an instrument point 131. The medical instrument 130, including the instrument point 131, has an instrument pattern 132. The instrument structure 103 has an instrument pattern 112.

An instrument structure locator 113 is attached to instrument structure 103. The instrument structure locator 113 features, aside from retro-reflective spheres 118, a mounting stand 133 with which the instrument structure locator 113 is attached to the instrument structure 103.

The medical instrument 130 features an instrument locator 135 which is located on the instrument end 134, which is across from the instrument point 131.

The medical instrument 130, shown here in FIG. 5, is an example of a body in the form of a medical instrument 130, which features multiple patterns 112, 132 and locators 113, 135.

The mobile tracking system 102 can unambiguously determine the geometry of the medical instrument 130 using the different patterns 112, 132. Furthermore, the mobile tracking system 102 determines the locator positions of the respective pattern 112, 132 on the medical instrument 130. This has the benefit that the position of the instrument point 131 is known with the measurement of the locators 113, 135.

As shown in FIG. 6, a structure 203 with a pattern 212 is attached to the bone piece 240. Structure 203 consists, in this implementation variation, a first support 241, a second support 242, and a third support 243.

Additionally, structure 240 contains a screw 244, so that structure 203 can be screwed on to the bone piece 240 in a way in which it is especially robustly attached to bone piece 240. In the example at hand, structure 203 is designed as a two dimensional plate onto which the pattern 212 is attached.

The landmark 350 shown in FIG. 7 is glued to the skin 351 of a patient. Landmark 350 has a funnel-shaped indentation 352. A structure 303 is inserted into the funnel-shaped indentation 352 of landmark 350. Structure 303 features a pattern 312. The attachment of structure 303 to landmark 350 occurs by use of a magnet 353. Magnet 353 of structure 302 works together with a ferromagnetic material 354 of landmark 350. An surgery cloth is clamped between landmark 350 and structure 302.

The medical instrument 430 shown in FIG. 8 contains an instrument insert 460, which features a three-dimensionally deformable element 461 between an instrument point 431 and an instrument end 434. Except for the deformable element 461, the instrument insert 460 is provided with an instrument pattern 432.

It is understood that in a further embodiment only a single partial region can be provided with such patterns.

At the instrument end 434, an instrument locator 435 is provided. Furthermore, an instrument structure locator 413 is fastened onto medical instrument 430. The instrument locator 435 as well as the instrument structure locator 413 contain retro-reflective spheres 418 (only numbered exemplarily here).

A mobile tracking system 402 with three cameras 405 (only explicitly numbered here) is located in the immediate vicinity of medical instrument 430. All patterns 432 and locators 413, 435 located on medical instrument 430 are measured with the mobile tracking system 402. A movement of instrument point 431 relative to further regions of the medical instrument 430 can be acquired and determined, for example.

Implant 565, shown in FIG. 9, contains a first deformable element 561A and a second deformable element 561B. Through this, implant 565 is divided into a first subdivision 566, a second subdivision 567, and a third subdivision 568. The individual subdivisions 566, 567, and 568 are therefore movable relative to each other. In order to detect and determine the complete implant geometry of implant 565, the whole implant 565 is covered with a pattern 520.

Implant 565 can be deformed and measured by a mobile tracking system until it has a desired shape. Implant 565 can then be attached to a body part (not shown here) by means of attachment screws (not shown here).

FIG. 10 shows a structure 603 with a pattern 612 as well as a bone locator 616 with retro-reflective spheres 618 which are all attached to a bone piece 640. Bone piece 640, structure 603, and bone locator 616 are measured by means of a mobile tracking system 602 which features cameras 605 (only numbered exemplarily here).

Since structure 603 with pattern 612 is partially covered by bone piece 640 so that pattern 612 cannot be directly detected by mobile tracking system 602 a mirror 670 is arranged across from pattern 612. Therefore, the mobile tracking system 602 can see and measure pattern 612 on structure 603 using the mirror 670.

In order to be identified, mirror 670 contains a marked border area 671 as well as an identifier 672 and further patterns 620 (only exemplarily numbered here).

A bone structure 714 with a pattern 715 is attached to the bone piece 740 as shown in FIG. 11. In the immediate vicinity of bone piece 740 there is a mobile tracking system 702 with three cameras 705 (only exemplarily numbered here).

Furthermore, in the immediate vicinity of bone piece 740 there is a hand held optical scanner 775 which measures the surface topology of bone piece 740 with a light beam 776. The orientation and position of the optical scanner 775 and the bone structure 714 is measured by means of the mobile tracking system 702. For this, the optical scanner 775 features three active LEDs 777 (only exemplarily numbered here). The surface topology of bone piece 740 which is measured by the optical scanner 765 is additionally referenced with already available CT- or MRI-images.

A bone structure 814 with a pattern 815 and a secondary pattern 883 is attached to bone piece 840, shown in FIG. 12. The secondary pattern 883 can be identified by a CT (not shown here), so that the spatial position of the secondary pattern 883 in relation to bone piece 840 is known based on the data obtained from the CT. A mobile tracking device 802 with three cameras 805 (only exemplarily numbered here) is held in front of bone piece 840.

A projector 880, which projects multiple spatially defined light rays 881 (only exemplarily numbered here) onto bone piece 840, is also held in the direct vicinity of bone piece 840. Projector 880 contains three active LEDs 877 (only exemplarily numbered here), in order to be able to be accurately measured by the mobile tracking system 802 regarding its spatial position. The regions of the bone piece 840 additionally illuminated by the light rays 881 are measured by the mobile tracking system 802 and computed as a spatial positions. The surface topology of bone piece 840 acquired from this procedure can be referenced with CT or MRI images.

FIG. 13 shows a bone structure 914 with a pattern 915 and a secondary pattern 983 which is attached to bone piece 940. A mobile tracking system with three cameras 905 (only exemplarily numbered here) is held in the direct vicinity of bone piece 940. The pattern 915 and therefore the secondary pattern 983 are detectable by means of the mobile tracking system 902. In addition, the secondary pattern 983 can be identified by further imaging systems (not shown here), like, for instance, CT or MRI devices. An ultrasound measurement head 985 measures bone piece 940 by means of sonic pulses 986. The ultrasound measurement head 985 contains three active LEDs 977 (only exemplarily numbered here), in order to be identified by the mobile tracking system 902. The bone surface measured by the ultrasound transducer head 985 and the bone structure are referenced in relation to CT or MRI images.

The mobile tracking system 1002 shown in FIG. 14 is attached to a medical tool 1090, which is, in this example, a drill with a drill insert 1090A. It is particularly beneficial for the mobile tracking system 1002 to be exceptionally small and light in order to be able to be unproblematically attached to the tool 1090.

The mobile tracking system 1002 contains a first light, small camera 1005 and a second light, small camera 1006, which both have an optical aperture angle 1091 (only exemplarily shown here).

Acquired measurement data is sent over a communication connection 1011A to an analysis and display device 1011. The communication connection 1011A, in this example, also contains the energy source (not shown here) for the tool 1090 and a water supply (not shown here) used to rinse a local area of work 1017 on tool 1090.

An alternative embodiment variation can provide for the optics (not explicitly shown here) of cameras 1005, 1006 to be attached to tool 1090 and the remaining components of cameras 1005, 1006, like, for example, an area sensor (not shown here), to be contained in the analysis and display device 1011. The cameras 1005, 1006 are optically connected with the area sensors by means of the communication connection 1011A, which, in the example at hand, consists of a fiber optic cable bundle.

The mobile tracking system 1002 at hand measures a jaw sector 1092 during an intervention. A first illumination 1007 as well as a second illumination 1008 provide for a sufficient illumination of structure 1003 (only exemplarily numbered here) which has a pattern 1012 (only exemplarily numbered here) as well as a secondary pattern 1083 (only exemplarily numbered here) in addition to teeth 1093 (only exemplarily numbered here), which are arranged in the jaw sector 1092.

The structures 1003 are attached to suitable teeth 1093 in this embodiment variation. Consequently, the secure hold of the structures 1003 on the teeth 1093 is ensured.

The mobile tracking system 1002 is oriented based on the structures 1003 which are temporarily attached to suitable teeth 1093 and contain appropriate patterns 1012.

It is particularly beneficial that the use of locators is no longer required because of the structures 1003 with the attached patterns 1012 and secondary patterns 1083.

Alternatively, a template 1094 which was created before the intervention and contains template patterns 1094A can be used. The template 1094 is attached to individual teeth 1093 of a lower jaw 1095 or an upper jaw (not shown here). The template 1094 has a preparation position for the medical tool 1090, in the example at hand.

If necessary, the structures 1003 must be anchored directly in the jaw bone 1095 (only the lower jaw is shown here). If the geometry of tool 1090 with the optional insert 1090A must be calibrated with respect to the mobile tracking system 1002, tool 1090 is connected in a defined mechanical manner with a calibration device (not shown here) which contains structures 1003. Mobile tracking system 1002 then determines, by means of these structures 1003, the relative spatial position to the calibration device and, from these measurements, the geometry of tool 1090 with the optional insert 1090A. The position of a drill bit 1090B and the orientation of the drill axis 1090C, for example, is then known relative to the mobile tracking system 1002.

Particularly during the positioning of tooth implants (not explicitly shown here) the initial position 1096 of the drill 1090A, the drill axis 1090C and a drill depth is obtained from further patient information. A corresponding method is described below.

The optimal configuration of an implant and a crown for a patient, like, for instance, the shape, color, position or force distribution of a replacement tooth on the implant in the bone are essentially based on the surface and the volume structure of the existing tooth rows, the jaws, and the soft tissue. These details are won through optical scanning and with three-dimensional measurement of the corresponding body parts using X rays.

After the optical scanning of the corresponding body parts, the structures 1003, containing the patterns 1012 and the X ray opaque secondary patterns 1083, are attached to certain teeth 1093. These structures 1003 can be templates 1094 or structures 1003 which are directly attached to certain teeth 1093. The patterns 1012 and secondary patterns 1083 can also be directly imprinted onto the teeth 1093.

Three-dimensional structures of bones 1095, teeth 1093, or the course of nerve pathways as well as the secondary patterns 1083 are measured by means of X ray radiation. The data of the optical scan (surface) as well as the X ray measurements (jaw and tooth structure) are transferred into a common coordinate system. Through this, a model of the considered body part is established, in which all necessary details are contained, like the bone structure 1095, the teeth 1093, the nerve pathways, the surfaces of soft tissue, the patterns 1012, and the secondary patterns 1083. In particular, a coordinate system of the mobile tracking system shows the positions of the jaw bone 1095, the teeth 1093, and the surfaces of soft tissue by measuring the patterns 1012.

With the aid of this model, the optimal configuration of the implant and the crown as well as the starting position 1096 of the drill 1090A, the drill axis 1090C, and the drill depth are established.

The implant is usually produced beforehand. The crown is created afterwards by suitable means, beneficially in the same surgery room and from semi-finished pieces and aided by CAD/CAM software. For this, no mold is needed for the production of the crown, as it is in current state-of-the-art applications.

During the completion of the crown, the actual main surgical treatment is performed. A software for the navigation with the mobile tracking system 1002 determines the start position 1096 of the drill 1090A, the drill axis 1090C, and the drill depth in the coordinate system of the mobile tracking system 1002. The mobile tracking system 1002 continuously determines the spatial position between the drill 1090A and the jaw anatomy. This information can be made available through acoustic and/or optical signals, for example. The surgeon can continuously use this information during the drill procedure. Alternatively, he can only use them during a critical phase, like, for example, at the beginning and/or in the end phase of the intervention.

The implant can be screwed into the prepared hole directly after the drilling procedure. Subsequently, the crown, which was finished in the mean time, is attached to the implant and the surgery area is further looked after.

This method is beneficially designed so that the optical scanning, the attachment of structures 1003 with the patterns 1012, 1083, the three-dimensional measurement of bones 1095 and teeth 1093 by means of X ray radiation, the establishing of a model of the body part, the optimal configuration of the implant and the crown, the production of the crown, the hole drilled with the help of the mobile tracking system 1003, the implantation of the implant, and the attachment of the crown can occur in one session.

It must be ensured that nerves (for example) are not damaged, in particular concerning jaw surgery, like the implantation of an implant. Therefore, aids like navigation systems based on tracking systems are proven to be of value. These help the surgeon work purposefully during an intervention. The method described in detail here advantageously functions without retro-reflective spheres.

The mobile tracking system 1102 shown in FIG. 15 is preferably implemented in minimally invasive surgery techniques. The local area of operation 1117 is uncovered by a small opening 1200 in minimally invasive surgery techniques. This means that the actual local area of work 1117 for the mobile tracking system 1102 is relatively small, which justifies the use of geometrically small tracking systems. The surgeon utilizes the mobile tracking system 1102 locally and depending on need. This means that the mobile tracking system 1102 is used before and after certain work steps. This is beneficial, as it can be put aside when not in use and therefore does not take up any space in the direct vicinity of the operation. If required, the mobile tracking system 1102 can be used in critical phases during a work step.

The typical procedures of a minimally invasive operation in which no registration is required, can take place as follows. A small opening 1200 is uncovered. Subsequently, structures 1103 (only exemplarily numbered here) with their patterns 1112 are suitably attached to joint bones 1104. The relative spatial position of the structures 1103 relative to their original position is measured. The surgical operation then takes place with the possible installation of aiding implants (not shown here). Furthermore, the definite implant (not shown here) is inserted and a measurement and assessment of the spatial position of the structures 1103 is again performed. Finally, all structures 1103 are removed.

The tracking system 1102 described here is ergonomically well developed. Additionally, it is economically priced. By means of the structures used here it is unnecessary to utilize cumbersome locators.

In all methods described above, instruments, tools, and/or aids, particularly like those explained in the following images, can be implemented.

At this point it is again mentioned that the described device and the described methods are not at all restricted to medical technology. The method at hand is also suited in particular for measurement and production technology as well as for the handling or processing of objects or bodies and in the field of quality control.

LIST OF REFERENCE SYMBOLS

1 Layout
2 Mobile tracking system
3 Structure
4 Bone
5 First camera
6 further camera
7 First light
8 further light
9 Handle
10 Activation switch
11 Analysis and display device
11A Communication connection
12 First pattern
13 First locator
14 further structure
15 further pattern
16 Bone locator
17 Local work area
18 Retro-reflective sphere
20 Pattern
21 Subdivision
22 Optional subdivision
23 Lines
25 Further patterns
26 Further patterns 101 Layout
102 Mobile tracking system
103 Structure
105 Cameras
112 Instrument structure pattern
113 Instrument structure locator
118 Retro-reflective spheres
130 Medical instrument
131 Instrument tip
132 Instrument pattern
133 Mounting stand
134 Instrument end
135 Instrument locator
203 Structure
212 Pattern
240 Bone piece
241 First support
242 Second support
243 Third support
244 Screw
303 Structure
312 Pattern
350 Landmark
351 Skin
352 Funnel-shaped depression
353 Magnet
354 Ferromagnetic material
355 Operation cloth
402 Mobile tracking system
405 Cameras
413 Instrument structure locator
418 Retro-reflective spheres
430 Medical instrument
431 Instrument tip
434 Instrument end
435 Instrument locator
461 Deformable section
460 Instrument insert
520 Pattern
561A First deformable element
561B Second deformable element
565 Implant
566 First subdivision
567 Second subdivision
568 Third subdivision
602 Mobile tracking system
603 Structure
605 Cameras
612 Pattern
616 Bone locator
618 Retro reflective spheres
620 Pattern
640 Bone piece
670 Mirror
671 Marked border area
672 Identifier
702 Mobile tracking system
705 Three cameras
714 Bone structure
715 Pattern
740 Bone piece
775 Optical scanner
776 Light ray
777 Three active LEDs
802 Mobile tracking system
805 Three cameras
814 Bone structure
815 Pattern
840 Bone piece
877 Three active LEDs
880 Projector
881 Light ray
883 Secondary pattern
902 Mobile tracking system
905 Three cameras
914 First bone structure
915 Pattern
940 Bone piece
977 Three active LEDs
983 Secondary pattern
985 Ultrasound transducer head
986 Sonic pulses
1002 Mobile tracking system
1003 Attached Structures
1005 First light, small camera
1006 Second light, small camera
1007 First light
1008 Second light
1011 Analysis and display device
1011A Communication connection
1012 Pattern
1017 Local work area
1083 Secondary pattern
1090 Medical tool
1090A Drill bit
1090B Drill tip
1090C Drill axis
1091 Optical aperture angle
1092 Jaw area
1094 Template
1094A Template pattern
1095 Lower jaw
1096 Start position
1097 Device which three-dimensionally measures bones and teeth by means of X-ray radiation
1102 Mobile tracking system
1103 Structures
1104 Bones
1112 Patterns
1117 Local area of work
1200 Small opening

The invention claimed is:
1. Measuring system for non-tactile localization and measurement of a spatial position and spatial orientation of bodies via a mobile optical tracking system, which localizes and identifies bodies and establishes relations among them, comprising:
 (a) at least parts of said mobile optical tracking system containing optics and area sensors suitable for relocation by hand and for usage in a mobile way;
 (b) at least two cameras with said optics and said area sensors;
 (c) at least one first pattern on a first structure and at least one second pattern on a second structure;
 (d) said first and second structures are attached to first and second bodies, respectively;
 (e) said at least one first pattern and said at least one second pattern being recognizable and analyzable by said mobile optical tracking system;
 (f) said at least one first pattern and said at least one second pattern are an entity made up of a combination of a selection of lines, circles, ellipses, triangles, and rectangles;

(g) said at least one first pattern and said at least one second pattern are suited for a spatial position and a spatial orientation of said first and second bodies; and (h) said at least one first pattern and said at least one second pattern are suited for identification of said first and second bodies.

2. The measuring system according to claim 1, wherein said mobile optical tracking system is being held portably relative to the bodies during its operation and during its use respectively.

3. The measuring system according to claim 1, wherein said mobile optical tracking system is arranged and/or held displaceably relative to be bodies during its operation and during its use respectively.

4. The measuring system according to claim 1, wherein said mobile optical tracking system is arranged free in space or stationary relative to the bodies.

5. The measuring system according to claim 1, wherein said mobile optical tracking system comprises a handle with which the said mobile optical tracking system is manually held and/or manually guided.

6. The measuring system according to claim 1, wherein said mobile optical tracking system comprises an activation apparatus with a switch or a button for starting and carrying through an acquisition and a measurement.

7. The measuring system according to claim 6, wherein said activation apparatus comprises means for voice control.

8. The measuring system according to claim 1, wherein said mobile optical tracking system comprises an attachment mechanism to connect it to a body or to a movable guidance mechanism, like a manually movable arm and/or robot arm.

9. The measuring system according to claim 1, wherein said mobile optical tracking system comprises means for wireless communication.

10. The measuring system according to claim 1, wherein said mobile optical tracking system comprises means for illumination comprising at least one LED with emission spectrum in the hyper-red range.

11. The measuring system according to claim 1, wherein said at least one first pattern is related to a secondary pattern by defined and fixed geometry.

12. The measuring system according to claim 11, wherein said secondary pattern is recognizable by a further imaging, in particular non-optical, system.

13. The measuring system according to claim 1, wherein said first structure is a technical structure in the field of medicine and said at least one first has known positions and/or geometrical details with respect to said technical structure in the field of medicine.

14. The measuring system according to claim 1, wherein said first structure is a part of a technical structure in the field of medicine.

15. The measuring system according to claim 14, wherein said technical structure in the field of medicine comprises deformable elements.

16. Method with the system according to claim 1 for non-contact determination and measurement of a space position and/or a space orientation of bodies with a tracking system by means of which the bodies are localized and brought into relation with one another comprising the movement and relocation of the mobile tracking system with respect to bodies during its usage either manually or automatically.

17. Method according to claim 16, wherein said mobile tracking system (2) is guided by hand during its usage.

18. Method according to claim 16, wherein said mobile tracking system (2) is held, in particular manually, directly in front of the local field of work with the relevant patterns (12, 15, 814, 815, 883, 1012, 1089, 1094A, 1103, 1112) during its usage.

19. Method according to claim 16, comprising the solely intermittent determination during the work steps of the space position and/or space orientation between at least two bodies (3, 4, 13, 16).

20. Method according to claim 16, comprising the start of a single shot, the start and/or the stop of a series of single shots or movie by means of said activation apparatus (10) for a determination and/or a measurement.

21. Method according to claim 16 comprising the step of determination and the measurement of the geometry of a said body (3, 4, 13, 16).

22. Method according to claim 16 comprising the step for registering of said bodies (3, 4, 13, 16) by means with attached patterns (12, 15) and/or with attached secondary patterns, which are recognized by further imaging systems.

23. Method according to claim 16, wherein said mobile tracking system (2) comprises its attachment to a body (1090), especially to a medical tool and/or a medical instrument.

24. Method according to claim 16, wherein said mobile tracking system (2) being attached to said body (3, 4, 13, 16) comprises the step of determination of the relative space position and/or relative space orientation with respect to one of said structures (3, 14) with at least one of the said patterns (12, 15) in real time.

25. Method according to claim 16 comprising the step of determination and measurement of the space position and/or space orientation of said locators (13, 16) being attached to said bodies (3, 4, 13, 16) with respect to said structures (3, 14) and/or said patterns (12, 15) being attached to said bodies (3, 13, 16).

26. Method according to claim 16 comprising the steps of:
(a) attaching to a body, like a work piece, a first structure with patterns and/or a first locator and attaching at least another structure with patterns and/or another locator;
(b) determination with a first measurement the relative space positions and/or the relative space orientations of the structures with the patterns and/or the locators with respect to each other by means of said system;
(c) treating of the body after the previous two steps;
(d) repeated determination with a at least one further measurement the relative space positions and/or the relative space orientations of the structures with the patterns and/or the locators with respect to each other;
(e) and by comparing the obtained relative space positions and/or the relative space orientations of the two measurements.

27. Method according to claim 26 comprising the step of treating of the treated body stepwise until the relative space position and/or the relative space orientation of the structures with the patterns and/or the locators as determined with the first measurement agree appropriately with the space position and/or the space orientation of the structures with the patterns and/or the locators as determined with the second measurement or with another predefined space position and/or the space orientation.

28. Method comprising the steps of
attaching patterns and/or secondary patterns onto at least one suitable bone, tooth or onto a template anchored in the jaw bone; a first measurement of the relative space positions and/or the relative space orientations of the patterns and/or the secondary patterns by means of the system according to claim 1, preferably with the tracking system affixed to a tool.

29. Method according to claim 28 comprising the step of optically scanning the surface of a local work area (1017) before executing said steps.

30. Method according to claim 28 comprising the step of measuring three-dimensionally the local work area (1017) by means of X-rays.

31. Method according to claim 28 comprising the step of establishing a three-dimensional model by means of the collected said optical scanning and said X-ray data.

32. Method according to claim 31 comprising a common coordinate system at least for the collected said optical scanning and said X-ray data in order to establish the said model.

33. Method according to claim 31 comprising the step of establishing the ideally optimal configuration of an implants and/or a crown by means of the said model.

34. Method according to claim 33 comprising the step of manufacturing of the said crown according to the said configuration by means of CAD/CAM support, essentially simultaneously with the surgical treatment with the drill.

35. Method according to claim 31 comprising the step of establishing the relative space positions and/or the relative space orientations of a drill bit (1090A), a drill axis (1090C), a drill depth and/or a start position (1096) by means of said model.

* * * * *